United States Patent [19]

Eteve

[11] Patent Number: 5,762,912
[45] Date of Patent: Jun. 9, 1998

[54] H₂O-RESISTANT SUNSCREEN/COSMETIC COMPOSITIONS COMPRISING HYDROPHILIC ACIDIC SPECIES

[75] Inventor: Martine Eteve, Paris, France

[73] Assignee: Société L'Oréal S.A., Paris, France

[21] Appl. No.: 425,049

[22] Filed: Apr. 19, 1995

[30] Foreign Application Priority Data

Apr. 19, 1994 [FR] France ................... 94 04634

[51] Int. Cl.⁶ .................... A61K 7/42; A61K 7/40
[52] U.S. Cl. .......................... 424/59; 424/60
[58] Field of Search .......................... 424/59, 60

[56] References Cited

U.S. PATENT DOCUMENTS

| | | | |
|---|---|---|---|
| 4,585,597 | 4/1986 | Lang et al. | 514/510 |
| 4,588,839 | 5/1986 | Lang et al. | 564/84 |
| 4,654,434 | 3/1987 | Lang et al. | 560/51 |
| 4,663,088 | 5/1987 | Lang et al. | 562/100 |
| 4,710,584 | 12/1987 | Lang et al. | 560/61 |

FOREIGN PATENT DOCUMENTS

| | | |
|---|---|---|
| 0390682 | 10/1990 | European Pat. Off. |
| 2185019 | 7/1987 | United Kingdom. |
| 2225013 | 5/1990 | United Kingdom. |

OTHER PUBLICATIONS

Patent Abstracts of Japan, vol. 12, No. 33 (C–472)(2880) Jan. 30, 1988 & JP–A–62 181 213, (Kao Corp) Aug. 8, 1987.

*Primary Examiner*—Shelley A. Dodson
*Attorney, Agent, or Firm*—Burns, Doane, Swecker & Mathis, L.L.P.

[57] ABSTRACT

Improvedly water-resistant sunscreen/cosmetic compositions, well suited for the prolonged UV-photoprotection of human skin and hair, comprise a cosmetically acceptable oil-in-water emulsion containing (i) at least one hydrophilic compound that screens ultraviolet irradiation and which comprises at least one optionally neutralized acid functional group, for example at least one optionally neutralized sulfonic acid or carboxylic acid functional group, and (ii) at least one insoluble filler material that is both inert with respect to said at least one hydrophilic acid compound (i) and an adsorbent therefor.

48 Claims, No Drawings

H₂O-RESISTANT SUNSCREEN/COSMETIC COMPOSITIONS COMPRISING HYDROPHILIC ACIDIC SPECIES

BACKGROUND OF THE INVENTION

1. Technical Field of the Invention

The present invention relates to novel sunscreen/cosmetic compositions useful in protecting the skin and the hair from ultraviolet radiation (compositions referred to hereinbelow more simply as "sunscreen" or "antisun" compositions) and having good resistance to water.

More especially, the present invention relates to water-resistant sunscreen/cosmetic compositions which are in the form of emulsions of the oil-in-water type and which contain, as photoprotective agents, hydrophilic UV screens comprising at least one acid radical in combination with adsorbent inert filler material. This invention also relates to the use of the aforesaid compositions for protecting human skin and/or hair against the deleterious effects of ultraviolet radiation.

2. Description of the Prior Art

It is known to this art that light radiation of wavelengths ranging from 280 nm to 400 nm promote tanning of the human epidermis, and that rays of wavelengths of from 280 to 320 nm, referred to as UV-B, cause erythema and burning of the skin which can impair the development of a natural tan; this UV-B radiation, hence, must be screened out.

It is also known to this art that UV-A irradiation, of wavelengths ranging from 320 to 400 nm, which effect tanning of the skin, are liable to induce adverse changes therein, in particular in the case of a sensitive skin or a skin continually exposed to solar radiation. UV-A rays cause, in particular, a loss of elasticity of the skin and the appearance of wrinkles leading to premature aging. They promote triggering of the erythematous reaction or exacerbate this reaction in some subjects, and can even be the source of phototoxic or photoallergic reactions. It is, therefore, desirable to screen out the UV-A radiation also.

Many cosmetic composition for the photoprotection (UV-A and/or UV-B) of the skin have to date been proposed to this art.

For various reasons associated especially with being more pleasant to use (gentleness, emollience, ease of application and the like) the antisun/sunscreen compositions currently available are typically oil-in-water emulsions (namely, a cosmetically acceptable vehicle, carrier or diluent) comprising an aqueous continuous dispersion phase and an oily discontinuous dispersed phase) which contain, at various concentrations, one or more conventional organic screens which are capable of selectively absorbing harmful UV radiation, these screens being selected as a function of the degree of desired protection. However, one of the problems presented by this type of sunscreen composition is, in particular, the fact that, once they have been applied to the skin in the form of a film by the users thereof, they have relatively little resistance to water.

It has also been proposed to improve the water resistance of the screening compositions by formulating them either with polymers, or else in a vehicle of the water-in-oil emulsion type, in the presence of emulsifying agents having a HLB (hydrophilic/lipophilic balance) ranging from 1 to 7, as described in U.S. Pat. Nos. 5,041,281 and 5,047,232.

The two techniques indicated above effectively permit improvement of the water resistance of the compositions when they contain lipophilic screens. The same is not, however, true in the case of compositions containing screens, in particular acidic screens, of hydrophilic nature, because the latter are very easily removed in water by bathing in the sea or in a swimming pool, in the shower or when engaging in water sports; thus, the sunscreen compositions which they contain, whether alone or combined with lipophilic screens, do not therefore provide the desired initial protection once the substrate (skin or hair) to which they have been applied has come into contact with water. It is then necessary to reapply the antisun product in order to retain suitable protection.

The above phenomenon is particularly critical and problematic when the antisun compositions are required to be in the form of oil-in-water emulsions. In the case of oil-in-water emulsions, or in the case of water-in-oil emulsions, the hydrophilic screens are present in the aqueous phase and the lipophilic screens are present in the fatty phase. As indicated above, oil-in-water emulsions are greatly preferred by the user to water-in-oil emulsions, in particular because of their pleasant feel (similar to water) and the fact that they are presented in the form of a lotion or of a nonoily cream; however, and unfortunately, it has also been found that they lose their UV protection efficiency much more easily once they come in contact with water, this decrease in the protection factor, caused by progressive loss to the water of the hydrophilic screen, moreover being increasingly notable, the greater the synergism in the degree of protection of the lipophilic/hydrophilic screening combination present in the antisun composition.

EP-A-0,275,719 describes sunscreen compositions containing acidic screens resistant to water by combining these with a fatty amine.

However, this solution is in certain instances unsatisfactory because it is impossible to combine certain acidic screens with fatty amides and also because fatty amines may elicit contact allergies, as is described in the text "Adverse Reactions to Cosmetics" (Anton de Cornelis de Groot—Ed. Rijksuniversiteit Groningen, 1988, chapter 5, p. 170 et seq.).

SUMMARY OF THE INVENTION

Accordingly, a major object of the present invention is the provision of novel sunscreen/cosmetic compositions comprising a hydrophilic screen including at least one acid moiety in an oil-in-water emulsion vehicle, and which have particularly improved water resistance.

Thus, it has now unexpectedly and surprisingly been found that the aforesaid objective and others are attained by combining in said vehicle the hydrophilic screen having an acidic moiety, with an inert insoluble filler material having adsorbent properties with respect to the screen.

By the term "water resistance" is intended the stability over time of the degree of protection in the UVA and/or UVB ranges of a antisun or sunscreen composition subjected (after application to the skin or to the hair) to contact with water. The solar protection associated with a given composition is characterized by assigning it a protection factor (or PF) which is mathematically expressed by the ratio of the exposure time necessary to attain the erythematous threshold with the UV screen to the time necessary to attain the erythematous threshold without UV screen.

Thus, the present invention features novel sunscreen/cosmetic compositions, comprising, in a cosmetically acceptable vehicle, carrier or diluent of the oil-in-water emulsion type, (i) at least one hydrophilic compound which screens ultraviolet radiation and includes at least one acid radical, and (ii) at least one insoluble filler material which is inert and adsorbent in respect of said acidic species.

The antisun or sunscreen compositions according to the invention, more fully described below, permit retention of sufficient protection factors even in the event of intentional or unintentional wetting of the parts of the body to which they have been applied. This is not only advantageous in economical terms, but further limits or eliminates the risk of accidental "sunburn" for users who forget to reapply the product to the body.

DETAILED DESCRIPTION OF BEST MODE AND PREFERRED EMBODIMENTS OF THE INVENTION

More particularly according to the present invention, the preferred hydrophilic screens contain at least one sulfonic acid radical, $SO_3H$. Nonetheless, this invention also comprehends compositions containing hydrophilic screens having a carboxylic acid radical, and others. The acid radical, whether carboxylic or sulfonic, may, moreover, be in a partially or totally neutralized state. Finally, it will be appreciated that, according to this invention, one or more hydrophilic screens comprising an acid functional group can, of course, also be used.

The inert adsorbent material which is used per the present invention and which does not per se exhibit photoprotective activity with respect to UV, is here useful only as a "trapping" substrate which can support and hold, at its surface and/or in the pore volume thereof, the hydrophilic screen including at least one acid radical, this being in order to limit or prevent dissolving of the latter when the antisun composition once applied to the skin and/or the hair, is contacted with water. This adsorbent substance, which is generally inorganic, advantageously has a specific surface area of at least 10 m²/g, preferably at least 50 m²/g and more preferably at least 100 m²/g. It is typically a powder whose mean particle size is at least 0.1 µm.

In a preferred embodiment of the present invention, the inert adsorbent filler material comprises a silica (or silicon dioxide) which may be fumed or precipitated, or else is a silica gel. Such silica is preferably fumed (pyrogenic silica). Such silicas are, in particular, marketed under the trademark AEROSIL® by Degussa; mong these latter, AEROSIL R 972 is more particularly preferred.

Other examples of adsorbent materials or substrates suitable for the present invention are aluminas (in particular active aluminas), aluminosilicates (in particular clays), mixed silicates of alkali and/or alkaline earth metals (smectites, Laponites®, in particular LAPONITES DS, D, XLS or XLG marketed by Laparte Industries, Ltd.), zeolites, talc, magnesia, and the like. Mixtures of fillers may, of course, also be used.

The above fillers may furthermore be subjected to specific surface treatments intended to make them more adsorbent with regard to a particular acidic water-soluble screen.

Exemplary acidic screens containing at least one $SO_3H$ group include, in particular, the sulfonic derivatives of 3-benzylidene camphor and in particular those having the following formulae (I), (II), (III), (IV) and (V):

Formula (I):

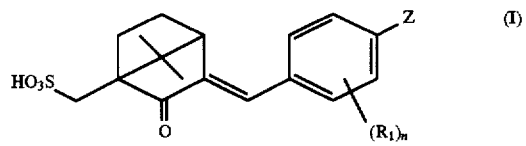

in which Z is a radical:

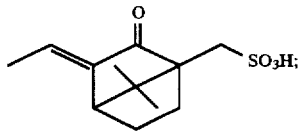

n is equal to 0 or is a integer ranging from 1 to 4 ($0 \leq n \leq 4$); and $R_1$ is one or more identical or different, linear or branched alkyl or alkoxy radicals having from about 1 to 4 carbon atoms.

A particularly preferred compound of formula (I) is that corresponding to n =0, namely, benzene-1,4-di(3-methylidenecamphor-10-sulfonic) acid.

Formula (II):

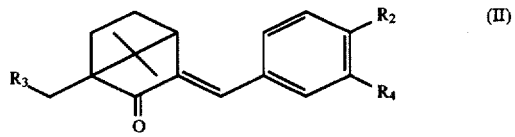

in which $R_2$ is a hydrogen atom, a halogen atom, an alkyl radical having about 1 to 4 carbon atoms or an —$SO_3H$ radical; and $R_3$ and $R_4$ are each a hydrogen atom or an —$SO_3H$ radical, at least one of the radicals $R_2$, $R_3$ or $R_4$ being an —$SO_3H$ radical, with the proviso that $R_2$ and $R_4$ cannot simultaneously be an —$SO_3H$ radical.

Particularly preferred compounds having formula (II) include those in which $R_2$ is the —$SO_3H$ radical in a position para to the benzylidene camphor and $R_3$ and $R_4$ are each a hydrogen atom, namely, 4-(3-methylidenecamphor)benzenesulfonic acid; or those in which $R_2$ and $R_4$ are each a hydrogen atom and $R_3$ is an —$SO_3H$ radical, namely, 3-benzylidenecamphor-10-sulfonic acid; or those in which $R_2$ is a methyl radical in a position para to the benzylidene camphor, $R_4$ is an —$SO_3H$ radical and $R_3$ is a hydrogen atom, namely, 2-methyl-5-(3-methylidenecamphor)benzenesulfonic acid; or those in which $R_2$ is a chlorine atom in a position para to the benzylidene camphor, $R_4$ is an —$SO_3H$ radical and $R_3$ is a hydrogen atom, namely, 2-chloro-5-(3-methylidenecamphor)benzenesulfonic acid; and those in which $R_2$ is a methyl radical in the position para to the benzylidene camphor, $R_4$ is a hydrogen atom and $R_3$ is an —$SO_3H$ radical, namely, 3-(4-methyl)benzylidenecamphor-10-sulfonic acid.

Formula (III):

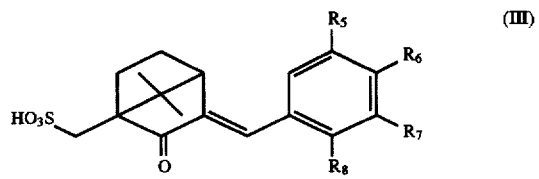

in which $R_5$ and $R_7$ are each a hydrogen atom, a hydroxyl radical, a linear or branched alkyl radical having about 1 to 8 carbon atoms, at least one of the radicals $R_5$ and $R_7$ being a hydroxyl, alkyl or alkoxy radical, and $R_6$ and $R_8$ are each a hydrogen atom, or a hydroxyl radical, at least one of the radicals $R_6$ and $R_8$ being a hydroxyl radical, with the proviso that, when $R_5$ and $R_8$ are each a hydrogen atom and $R_6$ is a hydroxyl radical, $R_7$ is other than an alkoxyl radical or a hydrogen atom.

Exemplary preferred compounds of formula (III) are those in which $R_5$ is a methyl radical, $R_6$ is a hydrogen atom, $R_7$ is a tert-butyl radical, and $R_8$ is a hydroxy radical, namely, 3-t-butyl-2-hydroxy-5-methylbenzylidenecamphor-10-sulfonic acid; or those in which $R_5$ is a methoxy radical, $R_6$ is a hydrogen atom, $R_7$ is a tert-butyl radical, and $R_8$ is a hydroxyl radical, namely, 3-t-butyl-2-hydroxy-5-methoxybenzylidenecamphor-10-sulfonic acid; or those in which $R_5$ and $R_7$ are each a tert-butyl radical, $R_6$ is a hydroxyl radical, and $R_8$ is a hydrogen atom, namely 3,5-di-tert-butyl-4-hydroxybenzylidenecamphor-10-sulfonic acid.

Formula (IV):

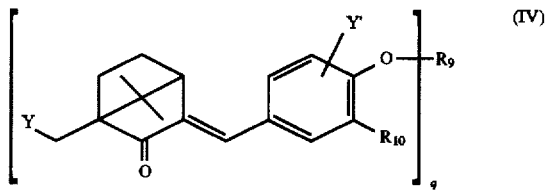

in which $R_9$ is a hydrogen atom, a linear or branched alkyl radical having from about 1 to 18 carbon atoms, a linear or branched alkenyl radical having from about 3 to 18 carbon atoms, a radical

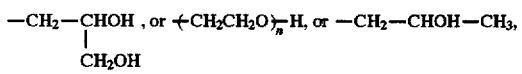

or else a divalent radical $-(CH_2)_m-$ or $-CH_2-CHOH-CH_2-$, wherein n is an integer ranging from 1 to 6 ($1 \leq n \leq 6$) and m is an integer ranging from 1 to 10 ($1 \leq m \leq 10$), $R_{10}$ is a hydrogen atom, an alkoxy radical having from 1 to 4 carbon atoms or a divalent —O— radical bonded to the $R_9$ radical when the latter is also divalent, g is an integer equal to 1 or 2, with the proviso that, if g is equal to 2, then $R_9$ must be a divalent radical, and Y and Y' are each a hydrogen atom or an —$SO_3H$ radical, with the further proviso that at least one of the radicals Y or Y' is other than a hydrogen atom.

Particularly exemplary compounds having the formula (IV) are those in which g is equal to 1, Y and $R_{10}$ are each a hydrogen atom, $R_9$ is a methyl radical and Y' in position 3- is an —$SO_3H$ radical, namely, 2-methoxy-5-(3-methylidenecamphor)benzenesulfonic acid; or those in which g is equal to 1, Y is an —$SO_3H$ radical, Y' is a hydrogen atom, and $R_{10}$ is a divalent —O— radical bonded to $R_9$ which is a methylene radical, namely, 3-(4,5-methylenedioxy)benzylidenecamphor-10-sulfonic acid; or those in which g is equal to 1, Y is an —$SO_3H$ radical, Y' and $R_{10}$ are each a hydrogen atom, and $R_9$ is a methyl radical, namely, 3-(4-methoxy)benzylidenecamphor-10-sulfonic acid; or those in which g is equal to 1, Y is an —$SO_3H$ radical, Y' is a hydrogen atom, $R_9$ is a methyl radical, and $R_{10}$ is a methoxy radical, namely, 3-(4,5-dimethoxy)benzylidenecamphor-10-sulfonic acid; or those in which g is equal to 1, Y is an —$SO_3H$ radical, Y' and $R_{10}$ are each a hydrogen atom and $R_9$ is an n-butyl radical, namely, 3-(4-n-butoxy)benzylidenecamphor-10-sulfonic acid; or those in which g is equal to 1, Y is an —$SO_3H$ radical, Y' is a hydrogen atom, $R_9$ is an n-butyl radical and $R_{10}$ is a methoxy radical, namely, 3-(4-n-butoxy-5-methoxy)benzylidenecamphor-10-sulfonic acid.

Formula (V):

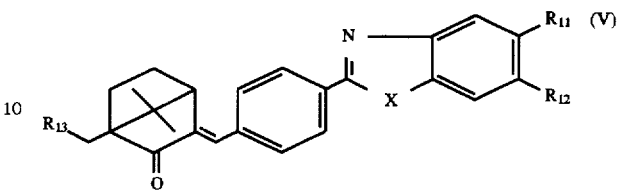

in which $R_{11}$ is a hydrogen atom or a linear or branched alkyl or alkoxy radical having from about 1 to 6 carbon atoms or an —$SO_3H$ radical, $R_{12}$ is a hydrogen atom or a linear or branched alkyl or alkoxy radical having from about 1 to 6 carbon atoms, $R_{13}$ is a hydrogen atom or an —$SO_3H$ radical, at least one of the radicals $R_{11}$ and $R_{13}$ being an —$SO_3H$ radical, and X is an oxygen or sulfur atom or a —NR— group, wherein R is a hydrogen atom or a linear or branched alkyl radical having from about 1 to 6 carbon atoms.

Particularly exemplary compounds of formula (IV) are those in which X is an —NH— radical, $R_{11}$ is an —$SO_3H$ radical and $R_{12}$ and $R_{13}$ are each a hydrogen atom, namely, 2-[4-(camphomethylidene)phenyl]benzimidazole-5-sulfonic acid.

The above compounds having the formulae (I), (II), (III), (IV), (V) are respectively described in U.S. Pat. No. 4,585,597 and FR-2,236,515, FR-2,282,426, FR-2,645,148, FR-2,430,938, and FR-2,592,380.

The screen having a sulfonic acid group may also be a sulfonic acid derivative of benzophenone having the following formula (VI):

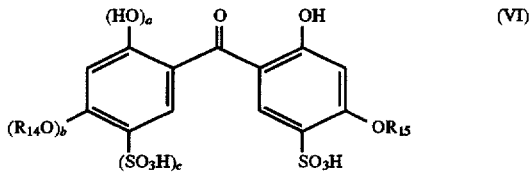

in which $R_{14}$ and $R_{15}$, which may be identical or different, are each a hydrogen atom or a linear or branched alkyl radical having from about 1 to 8 carbon atoms, and a, b and c, which may be identical or different, are each numbers equal to 0 or 1.

A particularly exemplary compound of formula (VI) is 2-hydroxy-4-methoxybenzophenone-5-sulfonic acid (compound of formula (VI) in which a, b, and c are equal to zero and $R_{15}$ is a methyl radical).

The screen having a sulfonic acid group may also be a sulfonic acid derivative of the following formula (VII):

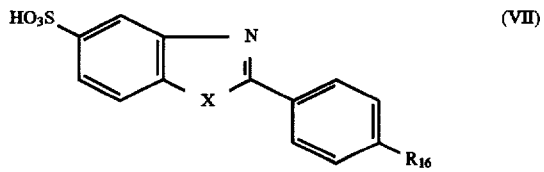

in which X is a hydrogen atom or an —NH— radical, $R_{16}$ is a hydrogen atom, a linear or branched alkyl or alkoxy radical having from about 1 to 8 carbon atoms or a radical of formula (VIII):

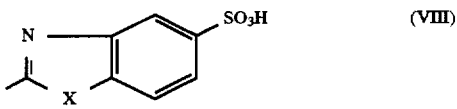

in which X' is an oxygen atom or an —NH— radical.

Particularly exemplary compounds of formula (VII) are those in which X is an —NH— radical and $R_{16}$ is a hydrogen atom, namely, 2-phenylbenzimidazole-5- sulfonic acid; X is an —NH— radical and $R_{16}$ is the group having formula (VIII) in which X' is the —NH— radical, namely, benzene-1,4-di(benzoxazol-2-yl-5-sulfonic) acid; X is an oxygen atom, and $R_{16}$ is the group having formula (VIII) in which X' is an oxygen atom, namely, benzene-1,4-di(benzoxazol-2-yl-5-sulfonic) acid.

The compounds of formula (VI) and (VII) are known compounds which can be prepared according to conventional techniques known to this art.

Exemplary preferred sunscreen/cosmetic compositions according to the present invention comprise the following combinations of an acidic hydrophilic UV screen and an adsorbent inert filler material:

(i) sulfonic acid derivative of 3-benzylidene camphor having formula (I) in which n=0 (benzene-1,4-di(3-methylidenecamphor-10-sulfonic) acid) and fumed (pyrogenic) silica of type AEROSIL R 972 marketed by Degussa;

(ii) sulfonic acid derivative of benzophenone having the formula (IV) in which a, b, and c are equal to 0 and $R_{15}$ is a methyl radical (2-hydroxy-4-methoxybenzophenone-5-sulfonic acid, in particular that marketed by BASF under the trademark Uvinul MS 40) and fumed (pyrogenic) silica of type AEROSIL R 972 marketed by Degussa; and (iii) sulfonic acid derivative of benzimidazole having formula (VII) in which X is the —NH— radical and $R_{16}$ is a hydrogen atom (2-phenylbenzimidazole-5-sulfonic acid, in particular that marketed by Merck under the trademark Eusolex 232) and fumed (pyrogenic) silica of type AEROSIL R 972 marketed by Degussa.

The hydrophilic UV screen comprising at least one acid radical, and in particular a sulfonic acid radical, is advantageously present in the sunscreen/cosmetic compositions according to the invention at a total composition ranging from approximately 0.2% to 10% by weight, and preferably from approximately 0.25% to 6% by weight, with respect to the total weight of the composition.

The adsorbent inert filler, and in particular silica, is advantageously present in the screening compositions in a content ranging from approximately 0.15% to 5%, and preferably from approximately 0.2% to 3%, with respect to the total weight of the composition.

The cosmetic compositions according to the invention may, of course, contain one or more hydrophilic or lipophilic complementary sunscreens which are active in the UVA and/or UVB ranges, which by definition are other than the acidic hydrophilic screens described above.

These complementary screens are preferably selected from among cinnamic derivatives such as, for example, 2-ethylhexyl p-methoxycinnamate, salicyclic derivatives such as, for example, 2-ethylhexyl salicylate and homomenthyl salicylate, derivatives of camphor such as, for example, 3(4-methylbenzylidene)camphor or 1,4-divinylbenzenecamphorsulfonic acid, derivatives of triazine such as 2,4,6-tris[p-(2'-ethylhexyl-1'-oxycarbonyl)anilino]1,3,5-triazine, derivatives of benzophenone such as 2-hydroxy-4-methoxybenzophenone, derivatives of dibenzoylmethane such as 4-tert-butyl-4'-methoxydibenzoylmethane, derivatives of $\beta,\beta'$-diphenylacrylates such as 2-ethylhexyl-α-cyano-$\beta,\beta'$-diphenylacrylate, derivatives of p-aminobenzoic acid such as, for example, octyl para-dimethylaminobenzoate, methyl anthranilate, and the screening polymers and screening silicones described in WO-93/04665. Other examples of such organic screens are described in EP-A-0,487,404.

The compositions according to the invention may also contain artificial agents for tanning and/or staining the skin (self-tanning agents) such as, for example, dihydroxyacetone (DHA).

The cosmetic compositions according to the invention may also contain coated or uncoated metal oxide nanopigments (mean size of the primary particles: generally from 5 nm to 100 nm, preferably from 10 to 50 nm) such as, for example, titanium, iron, zinc, zirconium or cerium oxide nanopigments which are photoprotective agents which are per se well known to this art and act by physical blocking (reflection and/or scattering) of UV radiation. Such coated or uncoated metal oxide nanopigments are, in particular, described in EP-A-0,518,772 and EP-A-0,518,773.

Also exemplary thereof are the products marketed under the trademarks UVT M 160, UVT M 212 and UVT M 262 by Kemira, and MT 100 SAS by Tayca.

The compositions of the invention may furthermore comprise cosmetic additives and adjuvants selected from among fats, organic solvents, nonionic thickeners, emollients, antioxidants, opacifying agents, stabilizers, silicones, antifoaming agents, moisturizers, vitamins, fragrances, preservatives, nonionic surfactants, fillers, sequestering agents, nonionic polymers, propellants, basifying or acidifying agents and dyes, pigments and colorants, or any other ingredient conventionally used in cosmetics, in particular for producing compositions in the form of emulsions.

Of course, one skilled in this art will take care to select this or these optional complementary compounds such that the advantageous properties intrinsically associated with the combination according to the invention are not, or substantially are not, detrimentally affected by the addition or additions contemplated.

The fats may comprise an oil or a wax or a mixture thereof, petrolatum, paraffin, lanolin, hydrogenated lanolin, acetylated lanolin, and they also comprise fatty acids, fatty alcohols such as lauric, cetylic, myristic, stearic, palmitic, oleic alcohol as well as 2-octyldodecanol, fatty acid esters such as glycerol monostearate, polyethylenegylcol monostearate, isopropyl myristate, isopropyl adipate, isopropyl palmitate, octyl palmitate, benzoates of $C_{12}$–$C_{15}$ fatty alcohols (Finsolv TN marketed by Finetex), polyoxypropylenated myristic acid having 3 moles of propylene oxide (WITCONOL APM marketed by Witco), trigylcerides of $C_6$–$C18$ fatty acids such as the trigylcerides of caprylic/capric acid, fluorinated and perfluorinated oils.

The oils may be selected from among animal, vegetable, mineral or synthetic oils and, in particular, hydrogenated palm oil, hydrogenated or nonhydrogenated castor oil, liquid petrolatum, liquid paraffin, Purcellin oil (stearyl octanoate), volatile or nonvolatile silicone oils, isoparafgfins and poly-α olefins.

The waxes may be selected from among animal, fossil, vegetable, mineral or synthetic waxes. Particularly exemplary thereof are beeswax, Carnauba, Candelilla, sugar cane or Japan wax, ozokerites, Montan wax, monocrystalline waxes, paraffins, silicone waxes and resins.

Exemplary organic solvents include the lower alcohols and polyols such as ethanol, isopropanol, propylene gylcol, glycerol and sorbitol.

The thickeners may be selected, in particular, from among crosslinked polyacrylic acids, modified or unmodified guar and cellulose gums such as hydropropylated guar gum, cetylhydroxyethylcellulose and hydroxypropylmethylcellulose.

The compositions of the invention are prepared according to techniques which are well known to this art for the synthesis of oil-in-water emulsions. During formulation of the composition, the acidic screen previously neutralized, for example by means of triethanolamine, is introduced into the fatty phase of the composition, and the adsorbent inert filler material for example silica, is then added to this fatty phase until a viscous liquid is obtained; the other constituents of the composition are then added and the composition is homogenized.

In the antisun/sunscreen emulsions according to the invention, intended for the protection of the skin, the aqueous phase is advantageously present at a ratio of approximately 50% to 95% by weight, with respect to the total weight of the formulation; the oily phase is advantageously present at a ratio of approximately 5% to 50% by weight, preferably approximately 10% to 30% by weight, with respect to the total weight of the formulation; and the (co)emulsifier(s) is (are) advantageously present at a ratio of approximately 0.5% to 20% by weight, preferably approximately 2% to 10% by weight, with respect to the total weight of the formulation.

The cosmetic compositions of the invention are useful for protecting the human epidermis or the hair against ultraviolet radiation, as antisun/sunscreen compositions or as make-up products (for the eyelashes, for the eyebrows, or for the skin).

These compositions may, depending on the applications envisaged, be in the form, for example, of a cream, a lotion, a cream gel, an ointment, a milk, a shampoo or any other hair composition to be rinsed out, intended to be applied before or after shampooing, before, during or after dyeing or bleaching, before, during or after a permanent wave or hair straightening, and, finally, may optionally be packaged as an aerosol and therefore be in the form of a mousse or spray.

The aqueous phase of the emulsion may comprise a non-ionic vesicular dispersion prepared according to known techniques (Bangham, Standish and Watkins, *J. Mol. Biol.*, 13, 238 (1965). FR-2-315,991 and FR-2,146,008).

The present invention, thus, also features a method for the cosmetic treatment of the skin or of the hair which is intended to protect these against the deleterious or damaging effects of UV radiation, comprising applying thereto an effective amount of a cosmetic composition as described above.

In order to further illustrate the present invention and the advantages thereof, the following specific examples are given, it being understood that same are intended only as illustrative and in nowise limitative.

EXAMPLE 1

| Sunscreen lotion for the skin (oil-in-water emulsion): | |
| --- | --- |
| (a) Mixture of cetylstearyl alcohol and cetylstearyl alcohol oxyethylenated with 33 moles of ethylene oxide, marketed under the trademark "Sinnowax AO" by Henkel | 7 g |
| (b) Mixture of non-self-emulsifiable glyceryl monostearate and distearate | 2 g |
| (c) Cetyl alcohol | 1.5 g |
| (d) Benzoate of $C_{12}$–$C_{15}$ alcohols (Finsolv TN Marketed by Finetex) | 10 g |
| (e) Silicone oil (Silbione oil 70 047 V 300 marketed by Rhône-Poulenc Silicones) | 1.5 g |
| (f) 4-Tert-butyl-4'-methoxydibenzoylmethane | 4 g |
| (g) 2-Ethylhexyl-2-cyano-3,3-phenylacrylate | 10 g |
| (h) Fumed or pyrogenic silica (Aerosil R 972 marketed by Degussa) | 0.5 g |
| (i) 2-Phenylbenzimidazole-5-sulfonic acid (Eusolex 232 marketed by Merck) | 3 g |
| (j) Triethanolamine | 2.21 g |
| (k) Glycerol | 5 g |
| (l) Fragrance, preservatives qs | |
| (m) Demineralized water qs for | 100 g |

The above emulsion was formulated by adding the fatty phase heated to approximately 80° C. to the aqueous phase containing glycerol and the preservatives, heated to the same temperature and under rapid agitation.

EXAMPLE 2

| Sunscreen cream for the skin (oil-in-water emulsion): | |
| --- | --- |
| (a) Mixture of cetylstearyl alcohol and cetylstearyl alcohol oxyethylenated with 33 moles of ethylene oxide, marketed under the trademark "Sinnowax AO" by Henkel | 7 g |
| (b) Mixture of non-self-emulsifiable glyceryl monostearate and distearate | 2 g |
| (c) Cetyl alcohol | 1.5 g |
| (d) Benzoate of $C_{12}$–$C_{15}$ alcohols (Finsolv TN marketed by Finetex) | 10 g |
| (e) Silicone oil (Silbione oil 70 047 V 300 marketed by Rhône-Poulenc Silicones) | 1.5 g |
| (f) 4-Tert-butyl-4'-methoxydibenzoylmethane | 2 g |
| (g) 2-Ethylhexyl-2-cyano-3,3-phenylacrylate | 10 g |
| (h) Fumed or pyrogenic silica (Aerosil R 972 marketed by Degussa) | 0.4 g |
| (i) Benzene-1,4-di(3-methylidene-camphor-10-sulfonic) acid | 1.98 g |
| (j) Triethanolamine | 1.84 g |
| (k) Glycerol | 5 g |
| (l) Fragrance, preservatives qs | |
| (m) Demineralized water qs for | 100 g |

The above emulsion was formulated by adding the fatty phase heated to approximately 80° C. to the aqueous phase containing glycerol and the preservatives, heated to the same temperature and under rapid agitation.

EXAMPLE 3

| Sunscreen cream for the skin (oil-in-water emulsion): | |
| --- | --- |
| (a) Mixture of cetylstearyl alcohol and cetylstearyl alcohol oxyethylenated with 33 moles of ethylene oxide, marketed under the trademark "Sinnowax AO" by Henkel | 7 g |
| (b) Mixture of non-self-emulsifiable glyceryl monostearate and distearate | 2 g |
| (c) Cetyl alcohol | 1.5 g |
| (d) Benzoate of $C_{12}$–$C_{15}$ alcohols (Finsolv TN marketed by Finetex) | 10 g |
| (e) Silicone oil (Silbione oil 70 047 V 300 marketed by Rhône-Poulenc Silicones) | 1.5 g |
| (f) 4-Tert-butyl-4'-methoxydibenzoylmethane | 4 g |

| Sunscreen cream for the skin (oil-in-water emulsion): | |
|---|---|
| (g) 2-Ethylhexyl-2-cyano-3,3-phenylacrylate | 10 g |
| (h) Fumed or pyrogenic silica (Aerosil R 972 marketed by Degussa) | 0.6 g |
| (i) Benzene-1,4-di(3-methylidene-camphor-10-sulfonic) acid | 2.97 g |
| (j) Triethanolamine | 2.31 g |
| (k) Glycerol | 5 g |
| (l) Titanium dioxide nanopigment coated with aluminum stearate and alumina (Micro Titanium Dioxide MT 100T marketed by Tayca) | 5 g |
| (m) Fragrance, preservatives qs | |
| (n) Demineralized water qs for | 100 g |

The above emulsion was formulated by adding the fatty phase heated to approximately 80° C. to the aqueous phase containing glycerol, the titanium dioxide nanopigment and the preservatives, heated to the same temperature and under rapid agitation.

EXAMPLE 4

| Sunscreen lotion for the skin (oil-in-water emulsion): | |
|---|---|
| (a) Mixture of cetylstearyl alcohol and cetylstearyl alcohol oxyethylenated with 33 moles of ethylene oxide, marketed under the trademark "Sinnowax AO" by Henkel | 7 g |
| (b) Mixture of non-self-emulsifiable glyceryl monostearate and distearate | 2 g |
| (c) Cetyl alcohol | 1.5 g |
| (d) Benzoate of $C_{12}$–$C_{15}$ alcohols (Finsolv TN marketed by Finetex) | 10 g |
| (e) Silicone oil (Silbione oil 70 047 V 300 marketed by Rhône-Poulenc Silicones) | 1.5 g |
| (f) 4-Tert-butyl-4'-methoxydibenzoylmethane | 1.5 g |
| (g) 3-(4-Methylbenzylidene)camphor (Eusolex 6300 marketed by Merck) | 4 g |
| (h) Fumed or pyrogenic silica (Aerosil R 972 marketed by Degussa) | 0.5 g |
| (i) Benzene-1,4-di(3-methylidene-camphor-10-sulfonic) acid | 1.98 g |
| (j) Triethanolamine | 1.44 g |
| (k) Glycerol | 5 g |
| (l) Titanium dioxide nanopigment coated with aluminum stearate and alumina (Micro Titanium Dioxide MT 100T marketed by Tayca) | 5 g |
| (m) Fragrance, preservatives qs | |
| (n) Demineralized water qs for | 100 g |

The above emulsion was formulated by adding the fatty phase heated to approximately 80° C. to the aqueous phase containing glycerol, the titanium dioxide nanopigment and the preservatives, heated to the same temperature and under rapid agitation.

EXAMPLE 5

| Sunscreen lotion for the skin (oil-in-water emulsion): | |
|---|---|
| (a) Mixture of cetylstearyl alcohol and cetylstearyl alcohol oxyethylenated with 33 moles of ethylene oxide, marketed under the trademark "Sinnowax AO" by Henkel | 7 g |
| (b) Mixture of non-self-emulsifiable glyceryl monostearate and distearate | 2 g |
| (c) Cetyl alcohol | 1.5 g |
| (d) Benzoate of $C_{12}$–$C_{15}$ alcohols (Finsolv TN marketed by Finetex) | 10 g |
| (e) Silicone oil (Silbione oil 70 047 V 300 marketed by Rhône-Poulenc Silicones) | 1.5 g |
| (f) 2-Ethylhexyl-p-methoxycinnamate | 7 g |
| (g) 2-Ethylhexyl-2-cyano-3,3-diphenylacrylate | 7 g |
| (h) 1,4-Divinylbenzene-β,β'-camphorsulfonic acid in aqueous solution at 33% | 9.09 g |
| (i) Synthetic smectite | 2 g |
| (j) Triethanolamine | 1.44 g |
| (k) Glycerol | 5 g |
| (l) Titanium dioxide nanopigment coated with aluminum stearate and alumina (Micro Titanium Dioxide MT 100T marketed by Tayca) | 3 g |
| (m) Fragrance, preservatives qs | |
| (n) Demineralized water qs for | 100 g |

The above emulsion was formulated by adding the fatty phase heated to approximately 80° C. to the aqueous phase containing glycerol, the titanium dioxide nanopigment and the preservatives, heated to the same temperature and under rapid agitation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A water-resistant sunscreen/cosmetic composition of matter, comprising a cosmetically acceptable oil-in-water emulsion containing (i) at least one hydrophilic compound that screens ultraviolet irradiation and which comprises at least one acid functional group or at least one neutralized acid functional group, and (ii) at least one insoluble filler material that is both inert with respect to said at least one hydrophilic acid compound (i) and an adsorbent therefor, and one specific surface area of same at least one insoluble filler material (ii) being at least 10 m²/g.

2. The sunscreen/cosmetic composition as defined by claim 1, said at least one hydrophilic acid compound (i) comprising at least one sulfonic acid functional group, or a neutralized sulphonic acid group.

3. The sunscreen/cosmetic composition as defined by claim 1, said at least one hydrophilic acid compound (i) comprising at least one carboxylic acid functional group, or a neutralized carboxylic acid functional group.

4. The sunscreen/cosmetic composition as defined by claim 1, said at least one hydrophilic acid compound (i) comprising a 3-benzylidene camphor compound.

5. The sunscreen/cosmetic composition as defined by claim 4, said at least one hydrophilic acid compound (i) having the following formula (I):

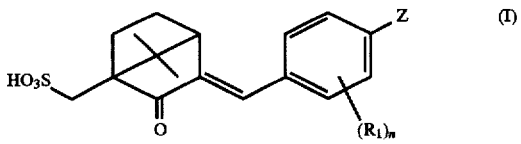

in which Z is a radical:

[structure: camphor-derived ketone with =CH- and -SO₃H substituents]

n is 0 or is an integer greater than or equal to 1 and less than or equal to 4, and the radicals $R_1$, which may be identical or different, are each a linear or branched alkyl or alkoxy radical having from about 1 to 4 carbon atoms.

6. The sunscreen/cosmetic composition as defined by claim 5, said compound of formula (I) being benzene-1,4-di(3-methylidenecamphor-10-sulfonic) acid.

7. The sunscreen/cosmetic composition as defined by claim 4, said at least one hydrophilic acid compound (i) having the following formula (II):

[structure of formula (II): benzylidene camphor with R₂, R₃, R₄ substituents]

in which $R_2$ is a hydrogen atom, a halogen atom, an alkyl radical having from 1 to 4 carbon atoms or an —SO₃H radical, $R_3$ and $R_4$ are each a hydrogen atom or an —SO₃H radical, at least one said radicals $R_2$, $R_3$ or $R_4$ being an —SO₃H radical, with the proviso that $R_2$ and $R_4$ cannot simultaneously be —SO₃H radicals.

8. The sunscreen/cosmetic composition as defined by claim 7, wherein formula (II), $R_2$ is an —SO₃H radical in a position para- to the benzylidene camphor and $R_3$ and $R_4$ are each a hydrogen atom.

9. The sunscreen/cosmetic composition as defined by claim 7, wherein formula (II), $R_2$ and $R_4$ are each a hydrogen atom and $R_3$ is an —SO₃H radical.

10. The sunscreen/cosmetic composition as defined by claim 7, wherein formula (II), $R_2$ is a methyl radical in a position para- to the benzylidene camphor, $R_4$ is an —SO₃H radical and $R_3$ is a hydrogen atom.

11. The sunscreen/cosmetic composition as defined by claim 7, wherein formula (II), $R_2$ is a chlorine atom in a position para- to the benzylidene camphor, $R_4$ is an —SO₃H radical and $R_3$ is a hydrogen atom.

12. The sunscreen/cosmetic composition as defined by claim 7, wherein formula (II), $R_2$ is a methyl radical in a position para- to the benzylidene camphor, $R_4$ is a hydrogen atom and $R_3$ is an —SO₃H radical.

13. The sunscreen/cosmetic composition as defined by claim 4, said at least one hydrophilic acid compound (i) having the following formula (III):

[structure of formula (III): benzylidene camphor with HO₃S and R₅, R₆, R₇, R₈ substituents]

in which $R_5$ and $R_7$, which may be identical or different, are each a hydrogen atom, a hydroxyl radical, a linear or branched alkyl radical having from 1 to 8 carbon atoms, or a linear or branched alkoxy radical having from 1 to 8 carbon atoms, at least one of the radicals $R_5$ and $R_7$ being a hydroxyl, alkyl or alkoxy radical, and $R_6$ and $R_8$, which may be identical or different, are each a hydrogen atom, or a hydroxyl radical, at least one of the radicals $R_6$ and $R_8$ being a hydroxyl radical, with the proviso that, when $R_5$ and $R_8$ are each a hydrogen atom and $R_6$ is a hydroxyl radical, then $R_7$ is other than an alkoxyl radical or a hydrogen atom.

14. The sunscreen/cosmetic composition as defined by claim 13, wherein formula (III), $R_5$ is a methyl radical, $R_6$ is a hydrogen atom, $R_7$ is a tert-butyl radical and $R_8$ is a hydroxy radical.

15. The sunscreen/cosmetic composition as defined by claim 13, wherein formula (III), $R_5$ is a methoxy radical, $R_6$ is a hydrogen atom, $R_7$ is a tert-butyl radical and $R_8$ is a hydroxyl radical.

16. The sunscreen/cosmetic composition as defined by claim 13, wherein formula (III), $R_5$ and $R_7$ are each a tert-butyl radical, $R_6$ is a hydroxyl radical and $R_8$ is a hydrogen atom.

17. The sunscreen/cosmetic composition as defined by claim 4, said at least one hydrophilic acid compound (i) having the following formula (IV):

Formula (IV):

[structure of formula (IV): benzylidene camphor with Y, Y', R₉, R₁₀ substituents]

in which $R_9$ is a hydrogen atom, a linear or branched alkyl radical having from 1 to 18 carbon atoms, a linear or branched alkenyl radical having from 3 to 18 carbon atoms, a group selected from among:

—CH₂—CHOH , or —(CH₂CH₂O)ₙ—H, or —CH₂—CHOH—CH₃,
         |
         CH₂OH or —(CH₂)ₘ— or —CH₂—CHOH—CH₂—, with n being an integer ranging from 1 to 6 (1≦n≦6) and m an integer ranging from 1 to 10 (1≦m≦10), $R_{10}$ is a hydrogen atom, an alkoxy radical having from 1 to 4 carbon atoms, or a divalent —O— radical bonded to the $R_9$ radical when $R_9$ is also divalent, g is an integer equal to 1 or 2, with the proviso that, if g is equal to 2, $R_9$ is necessarily a divalent radical, and Y and Y'are each a hydrogen atom or an —SO₃H radical, at least one of the radicals Y or Y'being other than a hydrogen atom.

18. The sunscreen/cosmetic composition as defined by claim 17, wherein formula (IV), g is equal to 1, Y and $R_{10}$ are each a hydrogen atom, $R_9$ is a methyl radical, and Y' is in position 3 and is an —SO₃H radical.

19. The sunscreen/cosmetic composition as defined by claim 17, wherein formula (IV), g is equal to 1, Y is an —SO₃H radical, Y'is a hydrogen atom, $R_{10}$ is a divalent —O— radical bonded to $R_9$ and $R_9$ is a methylene radical.

20. The sunscreen/cosmetic composition as defined by claim 17, wherein formula (IV), g is equal to 1, Y is an —SO₃H radical, Y' and $R_{10}$ are each a hydrogen atom, and $R_9$ is a methyl radical.

21. The sunscreen/cosmetic composition as defined by claim 17, wherein formula (IV), g is equal to 1, Y is an —SO₃H radical, Y' is a hydrogen atom, $R_9$ is a methyl radical and $R_{10}$ is a methoxy radical.

22. The sunscreen/cosmetic composition as defined by claim 17, wherein formula (IV), g is equal to 1, Y is an —SO$_3$H radical, Y' and R$_{10}$ are each a hydrogen atom, and R$_9$ is an n-butyl radical.

23. The sunscreen/cosmetic composition as defined by claim 17, wherein formula (IV), g is equal to 1, Y is an —SO$_3$H radical, Y' is a hydrogen atom, R$_9$ is an n-butyl radical and R$_{10}$ is a methoxy radical.

24. The sunscreen/cosmetic composition as defined by claim 4, said at least one hydrophilic acid compound (i) having the following formula (V):

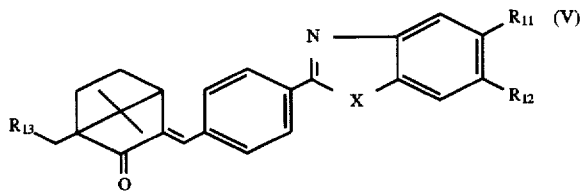

in which R$_{11}$ is a hydrogen atom or a linear or branched alkyl or alkoxy radical having from 1 to 6 carbon atoms or an —SO$_3$H radical, R$_{12}$ is a hydrogen atom or a linear or branched alkyl or alkoxy radical having from 1 to 6 carbon atoms, R$_{13}$ is a hydrogen atom or an —SO$_3$H radical, at least one of the radicals R$_{11}$ and R$_{13}$ being an —SO$_3$H radical, X is an oxygen or sulfur atom or a —NR— group, wherein R is a hydrogen atom or a linear or branched alkyl radical having from 1 to 6 carbon atoms.

25. The sunscreen/cosmetic composition as defined by claim 24, wherein formula (V), X is an —NH— radical, R$_{11}$ is an —SO$_3$H radical, and R$_{12}$ and R$_{13}$ are each a hydrogen atom.

26. The sunscreen/cosmetic composition as defined by claim 2, said at least one hydrophilic acid compound (i) having the following formula (VI):

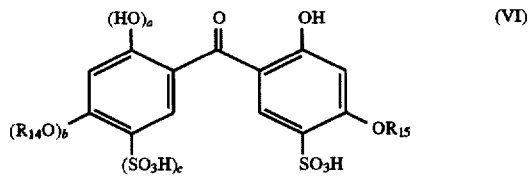

in which R$_{14}$ and R$_{15}$, which may be identical or different, are each a hydrogen atom or a linear or branched alkyl radical having from 1 to 8 carbon atoms, and a, b and c, which may be identical or different, are each equal to 0 or 1.

27. The sunscreen/cosmetic composition as defined by claim 26, wherein formula (VI), a=b=c=0 and R$_{15}$ is a methyl radical.

28. The sunscreen/cosmetic composition as defined by claim 2, said at least one hydrophilic acid compound (i) having the following formula (VII):

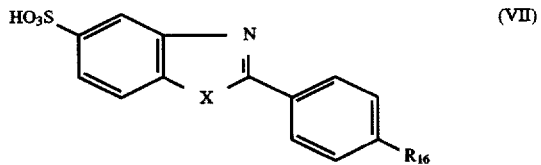

in which X is an oxygen atom or an —NH—— radical, R$_{16}$ is a hydrogen atom, a linear or branched alkyl or alkoxy radical having from 1 to 8 carbon atoms or a radical of the formula (VIII):

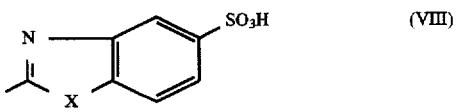

in which X' is, independently of X, an oxygen atom or an —NH— radical.

29. The sunscreen/cosmetic composition as defined by claim 28, wherein formula (VII), X is an —NH— radical and R$_{16}$ is a hydrogen atom.

30. The sunscreen/cosmetic composition as defined by claim 28, wherein formula (VII), X is an —NH— radical and R$_{16}$ is a radical of formula (VIII) wherein X' is an —NH— radical.

31. The sunscreen/cosmetic composition as defined by claim 28, wherein formula (VII), X is an oxygen atom and R$_{16}$ is the radical of formula (VIII) in which X' is an oxygen atom.

32. The sunscreen/cosmetic composition as defined by claim 1, said at least one inert adsorbent filler material (ii) comprising a silica, alumina, aluminosilicate, zeolite, talc or magnesia.

33. The sunscreen/cosmetic composition as defined by claim 32, said at least one inert adsorbent filler material (ii) comprising a fumed or precipitated silica, or a silica gel.

34. The sunscreen/cosmetic composition as defined by claim 1, comprising about 0.2% to 10% by weight of said at least one hydrophilic acid compound (i).

35. The sunscreen/cosmetic composition as defined by claim 1, comprising about 0.15% to 5% by weight of said at least one inert adsorbent filler material (ii).

36. The sunscreen/cosmetic composition as defined by claim 1, further comprising at least one complementary hydrophilic or lipophilic sunscreen active in the UVA and/or UVB ranges.

37. The sunscreen/cosmetic composition as defined by claim 36, said at least one complementary sunscreen comprising a cinnamate, salicyclate, benzylidene camphor compound, triazine compound, benzophenone compound, dibenzoyl methane compound, β,β'-diphenlacrylate compound, p-aminobenzoic acid compound, menthylanthranilate, screening polymer or screening silicone.

38. The sunscreen/cosmetic composition as defined by claim 37, said at least one complementary sunscreen comprising 4-tert-butyl-4'-methoxydibenxoylmethane, 2-ethylhexyl-2-cyano-3,3-diphenylacrylate or 3-(4-methylbenzylidene)camphor.

39. The sunscreen/cosmetic composition as defined by claim 1, further comprising a complementary photoprotective amount of coated or uncoated metal oxide nanopigments that physically block UV radiation.

40. The sunscreen/cosmetic composition as defined by claim 1, further comprising a cosmetically acceptable fat, organic solvent, nonionic thickener, emollient, antioxidant, opacifying agent, stabilizer, silicone, anti-foaming agent, moisturizer, vitamin, fragrance, preservative, nonionic surfactant, colorant, filler, sequestering agent, nonionic polymer, propellant, basifying or acidifying agent, or mixture thereof.

41. The sunscreen/cosmetic composition as defined by claim 1, the specific surface area of said at least one inert adsorbent filler material (ii) being at least 50 m$^2$/g.

42. The sunscreen/cosmetic composition as defined by claim 41, the specific surface area of said at least one inert adsorbent filler material (ii) being at least 100 m$^2$/g.

43. The sunscreen/cosmetic composition as defined by claim 34, comprising about 0.25% to 6% by weight of said at least one hydrophilic acid compound (i).

44. The sunscreen/cosmetic composition as defined by claim 35, comprising about 0.2% to 3% by weight of said at least one inert adsorbent filler material (ii).

45. The sunscreen/cosmetic composition as defined by claim 1, comprising a cream, lotion, gel, ointment, milk, mousse, spray, shampoo, or make-up.

46. The sunscreen/cosmetic composition as defined by claim 1, further comprising an artificial tanning agent.

47. A method for protecting human skin and/or hair against the deleterious effects of ultraviolet irradiation, comprising topically applying thereto an effective photoprotective amount of the sunscreen/cosmetic composition as described by claim 1.

48. A method for protecting human skin and/or hair against the deleterious effects of solar radiation, comprising topically applying thereto an effective photoprotective amount of the sunscreen/cosmetic composition as defined by claim 1.

* * * * *